United States Patent [19]

Shirai et al.

[11] Patent Number: 4,921,698
[45] Date of Patent: May 1, 1990

[54] POLYPEPTIDE HAVING GAMMA-INTERFERON ACTIVITY LACKING AMINO ACIDS CODED BY EXON 4

[75] Inventors: Takashi Shirai, Arcadia; R. Bruce Wallace, West Covine, both of Calif.

[73] Assignee: Asahi Kasei Kogyo Kabushiki Kaisha, Osaka, Japan

[21] Appl. No.: 105,473

[22] Filed: Sep. 30, 1987

Related U.S. Application Data

[63] Continuation of Ser. No. 614,130, May 25, 1984, abandoned.

[51] Int. Cl.$^5$ .................. A61K 45/02; C07K 15/26; C12P 21/00
[52] U.S. Cl. .................. 424/85.5; 530/351; 435/811
[58] Field of Search .................. 530/351; 424/85.5; 435/68

[56] References Cited

U.S. PATENT DOCUMENTS 4,604,284  8/1986  Kang et al. .................. 435/811

OTHER PUBLICATIONS

Gray et al., Nature, vol. 295, pp. 503–508, 1982.
Davis et al., Nucleic Acid Research, vol. 10, pp. 2487–2500, 1982.
Yujiro Higashi et al., "The Third Annual International Congress for Interferon Research", Miami, Fla., Nov. 1–3, 1982.
Capon et al., "The Third Annual International Congress for Interferon Research", Miami, Fla., Nov. 1–3, 1982.

*Primary Examiner*—Blondel Hazel
*Attorney, Agent, or Firm*—Birch, Stewart, Kolasch & Birch

[57] ABSTRACT

A polypeptide having gamma-interferon activity which lacks the amino acid sequence coded for by exon 4, a polynucleotide sequence which codes for said polypeptide, a replicable expression vehicle containing said polynucleotide sequence and a transformed microorganism containing said replicable expression vehicle are disclosed. The transformed microorganism is useful for preparing the polypeptide having gamma-interferon activity.

2 Claims, 17 Drawing Sheets

FIG. 4A pCG53

NUCLEOTIDE SEQUENCE

The nucleotide sequence is:

```
         10         20         30         40         50
TTCTCATGTT TGACAGCTTA TCATCGATAA GCTTTAATGC GGTAGTTTAT
<--pBR327

60         70         80         90        100
CACAGTTAAA TTGCTAACGC AGTCAGGCAC CGTGTATGAA ATCTAACAAT 110        120        130        140        150
GCGCTCATCG TCATCCTCGG CACCGTCACC CTGGATGCTG TAGGCATAGG 160        170        180        190        200
CTTGGTTATG CCGGTACTGC CGGGCCTCTT GCGGGATATC GTCCATTCCG 210        220        230        240        250
ACAGCATCGC CAGTCACTAT GGCGTGCTGC TAGCGCTATA TGCGTTGATG 260        270        280        290        300
CAATTTCTAT GCGCACCCGT TCTCGGAGCA CTGTCCGACC GCTTTGGCCG 310        320        330        340        350
CCGCCCAGTC CTGCTCGCTT CGCTACTTGG AGCCACTATC GACTACGCGA 360        370        380        390        400
                           BamHI
TCATGGCGAC CACACCCGTC CTGTGGATCC TTGGCTGTTT TGCTTGAGTA
                  pBR327--><--Gene complement 410        420        430        440        450
AGGTATCTCA AGGTCTACAA CAGCACCAGG CATGTAGTAG GTACTCCAGT 460        470        480        490        500
AAATATTTCT TGAGTGAAAG AATCAATTCG TACCACAATA TTATGAGGAA 510        520        530        540        550
CACACAATTA TTTTTCTTTT TCAGACAATA AAGCTGAAAC TTAGACAATA
```

FIG. 4B

```
         560        570        580        590        600
    TACATAATGT ATTAAAGGTC ACACTACTTG TAATGGAATA ACTTGGATTC
         610        620        630        640        650
    CAATCCAAGC CTTCTCCCTA GAGCTTACAC CCACTACTCC ACCCCCACTG
         660        670        680        690        700
    GTGTTTGCCA GCATTGGATG AGGGAGAGGA AGATTCTGAA ACGAGGGAGG
         710        720        730        740        750
    AAATAGGAAG GTGGAGAAGG GGCTAGAAAT AAATCTCTGT GTGCCAAGCT
         760        770        780        790        800
    AAGCAGTTTA AACTACATTC CATAGCAGAA CCTCTGAATT GAATAGTGAC
         810        820        830        840        850
    ATAATTAAAT CTGTATCTTA GAAAGATAAT TCAAAGAGCT GCTAACTGGA
         860        870        880        890        900
    AAAGCGAAAG CCAACAAAAT GCTAGTGGAA AGAAATACCA CATTTAATGG
         910        920        930        940        950
    AACCAAATGC AACTCTAAAA TTTTCACAGC TAAGAAGACT CCCCTCCCTA
         960        970        980        990       1000
    CTAATTCATT AATAGGTAGT TCTTTCACTC CAGGTCTCAC TTAGAAAAAG
        1010       1020       1030       1040       1050
    TCCAACACAG CATAAGTAGT TGTGAACTTA CACTTTATTC ATATATATTA
        1060       1070       1080       1090       1100
    GATATTGATA ATTTTAACAA ATGAGTTACT TTCCATTTGG GTACAGTCAC
        1110       1120       1130       1140       1150
    AGTTGTCAAC AATATTTGGA AGCACCAGGC ATGAAATCTC CTGAGATGCT
        1160       1170       1180       1190       1200
    ATGTTTTCAT CAGGGTCACC TGACACATTC AAGTTCTGTC TGACATGCCA
        1210       1220       1230       1240       1250
    TTAAAGCACT GGCTCAGATT GCAGGCATAT TTTCAAACCG GCAGTAACTG
        1260       1270       1280       1290       1300
    GATAGTATCA CTTCACTTAT AAGTGTTCAT TGTATCATCA AGTGAAATAA
        1310       1320       1330       1340       1350
    ACACACAACC CATGGGATCT TGCTTAGGTT GGCTGCCTAG TTGGCCCCTG
```

FIG. 4C

```
       1360       1370       1380       1390       1400
    AGATAAAGCC TTGTAATCAC ATAGCCTTGC CTAATTAGTC AGAAAACAAA 1410       1420       1430       1440       1450
    GGATTAAGTG AGACAGTCAC AGGATATAGG AATTATAAAT AATACATATA 1460       1470       1480       1490       1500
    TTAATAGATA TTCATTTTCA TTACACAAAA GTTGCTATTA TAAATACTTA 1510       1520       1530       1540       1550
    TTTGATTGAT GAGTCTAAAA ATATATTCCC CATATAAATA ATGTTAAATA 1560       1570       1580       1590       1600
    TTAATAAATA GATTTAGATT TAAAATTCAA ATATTGCAGG CAGGACAACC 1610       1620       1630       1640       1650
    ATTACTGGGA TGCTCTTCGA CCTCGAAACA GCATCTGACT CCTTTTTCGC
    <--Exon 4 complement 1660       1670       1680       1690       1700
    TTCCCTGTTT TAGCTGCTGG CGACAGTTCA GCCATCACTT GGATGAGTTC 1710       1720       1730       1740       1750
    ATGTATTGCT TTGCGTTGGA CATTCAAGTC AGTTACCTAT CGGGAAAGAA
                       Exon 4 complement--><--Intron 3

1760       1770       1780        1790       1800
    AAGAGCAAAA TTAATTTCAG GCATATAAGC CATCAGGATA TTCTGCTAAT 1810       1820       1830       1840       1850
    GTCATGATGG TCAGTGAAAA TAAAAGTATT CCTTTAAAAA ATGGACCTAC 1860       1870       1880        1890       1900
    TTTCTGGAGA ATAAATGCTT TGCAAGACCC TCGGCAATGA AACCAAAGAA 1910       1920       1930       1940       1950
    AGAATTTAAA TAGCCTCACC GAATAATTAG TCAGCTTTTC GAAGTCATCT
           Intron 3--><--Exon 3 complement 1960       1970       1980       1990       2000
    CGTTTCTTTT TGTTGCTATT GAAAAACTTG ACATTCATGT CTTCCTTGAT 2010       2020        2030       2040       2050
    GGTCTCCACA CTCTTTTGGA TGCTCTGGTC ATCTTTAAAG TTTTTAAAAA 2060       2070       2080       2090       2100
    GTTTGAAGTA AAAGGAGACA ATTTGGCTCT GCATTATTTT TCTGTCACTC
                                                Exon 3 complement-
```

FIG. 4D

```
       2110       2120       2130       2140       2150
   TCCTTGGAAG GAAAGAGCAC AAACAGAGGA TGATGTGAAT TTATCCATCA
   -><--Intron 2

2160       2170       2180       2190       2200
   GAAAGCAAGC AACAGGAAAA TTAGCCAAAT GGGAATATTC AGCTTACCTC
                                                Intron 2--><--Exon 2

2210       2220       2230       2240       2250
   TTTCCAATTC TTCAAAATGC CTAAGAAAAG AGTTCCATTA TCCGCTACAT
   complement                                           Exon 2260       2270       2280       2290       2300
   CTGAATGACC TGCATTCTAA AAAAAAAAAA GAAAAAATTG GTTTACAATT
    2 complement--><--Intron 1

2310       2320       2330       2340       2350
   AGCCCATAAA TTGCCTTAAA AATATATTTC AAGTTTCATT GAACTCAGAT 2360       2370       2380       2390       2400
   GTGACAATAT TCACTGATTT CCTTTTCAAC TCTTCTGCTT AGTTCTAACA 2410       2420       2430       2440       2450
   ATAAGTATTC CCAAAAGGCT TATGTGAGAT ATAGACAAAG ACTATTATGT 2460       2470       2480       2490       2500
   TCTTTTAGCT TTTTTATTTC CCAATATAAC CATTAAATTG CAATGTCACA 2510       2520       2530       2540       2550
   AATGATTATT TAGTCAAGGA ACTCATCTAG TCAATAATTA ACAAAATAAC 2560       2570       2580       2590       2600
   ACCAAATCTC AAAATGACTG CCTACAAGAG ATGACAGCCT ATCAGAGATG 2610       2620       2630       2640       2650
   CTACAGCAAG TCGATATTCA GTCATTTTCA ACCACAAACA AGTACTATTA 2660       2670       2680       2690       2700
   AAAAGTCATA CTTACAAAAT ATTTCTTAAG GTTTTCTGCT TCTTTTACAT
    Intron 1--><--Exon 1 complement 2710       2720       2730       2740       2750
   ATGGGTCCTG GCAGTAACAG CCAAGAGAAC CCAAAACGAT GCAGAGCTGA
       2760       2770       2780       2790       2800
   AAAGCCAAGA TATAACTTGT ATATTTCATC GTTTCCGAGA GAATTAAGCC
                                         5' Portion 2810       2820       2830       2840       2850
   AAAGAAGTTG AAATCAGTAG TTCTTGTATC AAGCTGATCA GGTCCAAAGG
```

FIG. 4E

```
        2860       2870       2880       2890       2900
   ACTTAACTGA TCTTTCTCTT CTAATAGCTG ATCTTCAGAT GATCAGAACA 2910       2920       2930       2940       2950
   ATGTGCTGCA CCTCCTCTGG CTGCTGGTAT TTATACCTAA TTGAAGTCTC
                                                GENCOM'

*  2960       2970       2980       2990       3000
   CTGGTCGACC GATGCCCTTG AGAGCCTTCA ACCCAGTCAG CTCCTTCCGG
   ---><--pBR327
```

FIG. 5A

SUMMARY OF EVENTS LEADING TO mp9-TGd1

```
      6420       6430       6440       6450       6460       6470       6480
   GATTCATTAA TCCAGCTGGC ACGACAGGTT TCCCGACTGG AAAGCGGGCA GTGAGCGCAA CGCAATTAAT
                                                                    <--------CAP 6490       6500       6510       6520       6530       6540       6550
   GTGAGTTACC TCACTCATTA GGCACCCCAG GCTTTACACT TTATGCTTCC GGCTCGTATG TTGTGTGGAA
   SITE---------------->           <------>                                 ↑<-
                                     -35                                   start
                                    sequence                           transcription 6560       6570       6580       6590       6600       6610       6620
                                                                             Sal
   TTGTGAGCGG ATAACAATTT CACACAGGAA ACAGCTATGA CCATGATTAC GCCAAGCTTG GCTGCAGGTC
   operator------------>
                         <---->     <->                   <------------------
                         Shine      beta-gal             linker restriction
                        Dalgarno    start                      region
                      3'CCTT TGTCGATAC5'
                      D-4 Deleter 1st half 6630       6640       6650       6660       6670       6680       6690
   L_
   GACTCAGGAG ACTTCAATTA GGTATAAATA CCAGCAGCCA GAGGAGGTGC AGCACATTGT TCTGATCATC
   -><--5' portion of the gene
      <--pCG53 insert 6700       6710       6720       6730       6740       6750       6760
   TGAAGATCAG CTATTAGAAG AGAAAGATCA GTTAAGTCCT TTGGACCTGA TCAGCTTGAT ACAAGAACTA 6770       6780       6790                   6813
   CTGATTTCAA CTTCTTTGGC TTAATTCTCT CGGAAACG ATG AAA TAT ACA AGT TAT ATC
                                              MET Lys Tyr Thr Ser Tyr Ile
             5' portion of gene--> <--exon 1

6828             6843             6858             6873
   TTG GCT TTT CAG CTC TGC ATC GTT TTG GGT TCT CTT GGC TGT TAC TGC CAG GAC
                                               3'ACA ATG ACG GTC CTG
                                                D-4 deleter 2nd half
   Leu Ala Phe Gln Leu Cys Ile Val Leu Gly Ser Leu Gly Cys Tyr Cys Gln Asp
```

FIG. 5B

```
              6888                 6903                      6922        6932
CCA TAT GTA AAA GAA GCA GAA AAC CTT AAG AAA TAT TTT GTAAGTATGA CTTTTTAATA
G5'
Pro Tyr Val Lys Glu Ala Glu Asn Leu Lys Lys Tyr Phe
                                                    exon 1--> <--intron 1 remainder 6942       6952       6962       6972       6982       6992       7002
GTACTTGTTT GTGGTTGAAA ATGACTGAAT ATCGACTTGC TGTAGCATCT CTGATAGGCT GTCATCTCTT 7012       7022       7032       7042       7052       7062       7072
GTAGGCAGTC ATTTTGAGAT TTGGTGTTAT TTTGTTAATT ATTGACTAGA TGAGTTCCTT GACTAAATAA 7082       7092       7102       7112       7122       7132       7142
TCATTTGTGA CATTGCAATT TAATGGTTAT ATTGGGAAAT AAAAAAGCTA AAAGAACATA ATAGTCTTTG 7152       7162       7172       7182       7192       7202       7212
TCTATATCTC ACATAAGCCT TTTGGGAATA CTTATTGTTA GAACTAAGCA GAAGAGTTGA AAAGGAAATC 7222       7232       7242       7252       7262       7272       7282
AGTGAATATT GTCACATCTG AGTTCAATGA AACTTGAAAT ATATTTTTAA GGCAATTTAT GGGCTAATTG 7292       7302                   7326                  7341
TAAACCAATT TTTTCTTTTT TTTTTTTAG AAT GCA GGT CAT TCA GAT GTA GCG GAT AAT
                                   Asn Ala Gly His Ser Asp Val Ala Asp Asn
      remainder intron 1--> <--exon 2

7356              7371                  7390         7400
GGA ACT CTT TTC TTA GGC ATT TTG AAG AAT TGG AAA GAG GTAAGCTGAA TATTCCCATT
Gly Thr Leu Phe Leu Gly Ile Leu Lys Asn Trp Lys Glu
                                                    exon 1--> <--intron 2 complete
       7410       7420       7430       7440       7450       7460       7470
TGGCTAATTT TCCTGTTGCT TGCTTTCTGA TGGATAAATT CACATCATCC TCTGTTTGTG CTCTTTCCTT
                                                                              intron 2

7490                7505                   7520
CCAAG GAG AGT GAC AGA AAA ATA ATG CAG AGC CAA ATT GTC TCC TTT TAC TTC
      Glu Ser Asp Arg Lys Ile MET Gln Ser Gln Ile Val Ser Phe Tyr Phe
      ---> <--exon 3

7535                7550                  7565               7580
AAA CTT TTT AAA AAC TTT AAA GAT GAC CAG AGC ATC CAA AAG AGT GTG GAG ACC ATC
Lys Leu Phe Lys Asn Phe Lys Asp Asp Gln Ser Ile Gln Lys Ser Val Glu Thr Ile 7595                7610                7625
AAG GAA GAC ATG AAT GTC AAG TTT TTC AAT AGC AAC AAA AAG AAA CGA GAT GAC
Lys Glu Asp MET Asn Val Lys Phe Phe Asn Ser Asn Lys Lys Lys Arg Asp Asp 7640              7655              7668       7678       7688       7698
TTC GAA AAG CTG ACT AAT TAT TCG GTGAGGCTAT TTAAATTCTT TCTTTGGTTT CATTGCCGAG
Phe Glu Lys Leu Thr Asn Tyr Ser
                               exon 3--> <--intron 3 remainder
```

FIG. 5C

```
        7708       7718       7728       7738       7748       7758       7768
    GGTCTTGCAA AGCATTTATT CTCCAGAAAG TAGGTCCATT TTTTAAGGA ATACTTTTAT TTTCACTGAC 7778       7788       7798       7808       7818       7828       7838
    CATCATGACA TTAGCAGAAT ATCCTGATGG CTTATATGCC TGAAATTAAT TTTGCTCTTT TCTTTCCCGA
                                                                      intron 3

7856                   7871                   7886
    TAG GTA ACT GAC TTG AAT GTC CAA CGC AAA GCA ATA CAT GAA CTC ATC CAA GTG
        Val Thr Asp Leu Asn
    --> <--exon 4

7901                   7916                   7931                   7946
    ATG GCT GAA CTG TCG CCA GCA GCT AAA ACA GGG AAG CGA AAA AGG AGT CAG ATG 7961                   7976       7986       7996       8006
    CTG TTT CGA GGT CGA AGA GCA TCC CAG TAA TGGTTGTCCT CCCTGCAATA TTTGAATTTT
                                 exon 4--> <--3' portion of the gene fragment
                              3'GT AGG GTC ATT ACCAGCTGGACG5'
                              23-mer Primer/Mutator
```

```
        8016       8026       8036       8046       8056       8066       8076
    AAATCTAAAT CTATTTATTA ATATTTAACA TTATTTATAT GGGAATATA TTTTTAGACT CATCAATCAA 8086       8096       8106       8116       8126       8136       8146
    ATAAGTATTT ATAATAGCAA CTTTTGTGTA ATGAAAATGA ATATCTATTA ATATATGTAT TATTTATAAT 8156       8166       8176       8186       8196       8206       8216
    TCCTATATCC TGTGACTGTC TCACTTAATC CTTTGTTTTC TGACTAATTA GGCAAGGCTA TGTGATTACA 8226       8236       8246       8256       8266       8276       8286
    AGGCTTTATC TCAGGGCCA ACTAGGCAGC CAACCTAAGC AAGATCCCAT GGGTTGTGTG TTTATTTCAC 8296       8306       8316       8326       8336       8346       8356
    TTGATGATAC AATGAACACT TATAAGTGAA GTGATACTAT CCAGTTACTG CCGGTTTGAA AATATGCCTG 8366       8376       8386       8396       8406       8416       8426
    CAATCTGAGC CAGTGCTTTA ATGGCATGTC AGACAGAACT TGAATGTGTC AGGTGACCCT GATGAAAACA 8436       8446       8456       8466       8476       8486       8496
    TAGCATCTCA GGAGATTTCA TGCCTGGTGC TTCCAAATAT TGTTGACAAC TGTGACTGTA CCCAAATGGA 8506       8516       8526       8536       8546       8556       8566
    AAGTAACTCA TTTGTTAAAA TTATCAATAT CTAATATATA TGAATAAAGT GTAAGTTCAC AACTACTTAT 8576       8586       8596       8606       8616       8626       8636
    GCTGTGTTGG ACTTTTTCTA AGTGAGACCT GGAGTGAAAG AACTACCTAT TAATGAATTA GTAGGGAGGG 8646       8656       8666       8676       8686       8696       8706
    GAGTCTTCTT AGCTGTGAAA ATTTTAGAGT TGCATTTGGT TCCATTAAAT GTGGTATTTC TTTCCACTAG
```

FIG. 5D

```
        8716       8726       8736       8746       8756       8766       8776
     CATTTTGTTG GCTTTCGCTT TTCCAGTTAG CAGCTCTTTG AATTATCTTT CTAAGATACA GATTTAATTA 8786       8796       8806       8816       8826       8836       8846
     TGTCACTATT CAATTCAGAG GTTCTGCTAT GGAATGTAGT TTAAACTGCT TAGCTTGGCA CACAGAGATT 8856       8866       8876       8886       8896       8906       8916
     TATTTCTAGC CCCTTCTCCA CCTTCCTATT TCCTCCCTCG TTTCAGAATC TTCCTCTCCC TCATCCAATG 8926       8936       8946       8956       8966       8976       8986
     CTGGCAAACA CCAGTGGGGG TGGAGTAGTG GGTGTAAGCT CTAGGGAGAA GGCTTGGATT GGAATCCAAG 8996       9006       9016       9026       9036       9046       9056
     TTATTCCATT ACAAGTAGTG TGACCTTTAA TACATTATGT ATATTGTCTA AGTTTCAGCT TTATTGTCTG 9066       9076       9086       9096       9106       9116       9126
     AAAAAGAAAA ATAATTGTGT GTTCCTCATA ATATTGTGGT ACGAATTGAT TCTTTCACTC AAGAAATATT 9136       9146       9156       9166       9176       9186       9196
     TACTGGAGTA CCTACTACAT GCCTGGTGCT GTTGTAGACC TTGAGATACC TTACTCAAGC AAAACAGCCA
                                                                      pOG53 insert- 9206       9216       9226       9236
     BamHI
     AGGATCCCCG GGAATTCACT GGCCGTCGTT TTACAACGTC
     -><-------------><--lac insert M13mp9
       linker restriction
            region
```

FIG. 6A mp9-TGA123-1

```
        6420       6430       6440       6450       6460       6470       6480
     GATTCATTAA TCCAGCTGGC ACGACAGGTT TCCCGACTGG AAAGCGGGCA GTGAGCGCAA CGCAATTAAT
                                                                     <———CAP 6490       6500       6510       6520       6530       6540       6550
     GTGAGTTACC TCACTCATTA GGCACCCCAG GCTTTACACT TTATGCTTCC GGCTCGTATG TTGTGTGGAA
     SITE——————————————>   <———>      <———>                              ↑<—
                                      -35                                 start
                                      sequence                            transcription 6560       6570       6580       6589 6859              6873
     TTGTGAGCGG ATAACAATTT CACACAGGAA ACAGCTATG  TGT TAC TGC CAG GAC CCA TAT GTA
     operator———————————————————>    lac—>      <—IFN exon 1
                                     <—>        MET Cys Tyr Cys Gln Asp Pro Tyr Val
                                     Shine      beta-gal
                                     Dalgarno   start 6888                                6912 7312                      7338
     AAA GAA GCA GAA AAC CTT AAG AAA TAT TTT  AAT GCA GGT CAT TCA GAT GTA GCG GAT
     Lys Glu Ala Glu Asn Leu Lys Lys Tyr Phe  Asn Ala Gly His Ser Asp Val Ala Asp
                                 exon 1—>   <—exon 2

7356                                 7380 7476              7490
                DdeI
     AAT GGA ACT CTT TTC|TTA GGC ATT TTG AAG AAT TGG AAA GAG  GAG AGT GAC AGA AAA
     Asn Gly Thr Leu Phe Leu Gly Ile Leu Lys Asn Trp Lys Glu  Glu Ser Asp Arg Lys
                                                 exon 2—> <—exon 3

7505            7520            7535          7547
     ATA ATG CAG AGC CAA ATT GTC TCC TTT TAC TTC AAA CTT TTT AAA AAC TTT AAA GAT
     Ile MET Gln Ser Gln Ile Val Ser Phe Tyr Phe Lys Leu Phe Lys Asn Phe Lys Asp 7565            7580            7595
     GAC CAG AGC ATC CAA AAG AGT GTG GAG ACC ATC AAG GAA GAC ATG AAT GTC AAG TTT
     Asp Gln Ser Ile Gln Lys Ser Val Glu Thr Ile Lys Glu Asp MET Asn Val Lys Phe 7610            7625            7640              7659
                                                     AluI
     TTC AAT AGC AAC AAA AAG AAA CGA GAT GAC TTC GAA AAG|CTg act aat tat tcg gtc
                                                              exon 3—
     Phe Asn Ser Asn Lys Lys Lys Arg Asp Asp Phe Glu Lys Leu Thr Asn Tyr Ser Val
```

FIG. 6B

```
               7777        7789       7800       7810       7820
act gac cat cat gac att agc aga ata tcc tga tggct tatatgcctg aaattaattt
      >  <—intron 3 remainder
Thr Asp His His Asp Ile Ser Arg Ile Ser  .

7830       7840       7850      7858  8406        8416       8426
tgctctttc tttcccgata ggtaactgac ttgaatgt    gtc aggtgaccct gatgaaaaca
                         <——exon 4———>     <—3' portion of gene fragment 8436       8446       8456       8466       8476       8486       8496
 DdeI
TAGCATC|TCA GGAGATTTCA TGCCTGGTGC TTCCAAATAT TGTTGACAAC TGTGACTGTA CCCAAATGGA 8506       8516       8526       8536       8546       8556       8566
AAGTAACTCA TTTGTTAAAA TTATCAATAT CTAATATATA TGAATAAAGT GTAAGTTCAC AACTACTTAT 8576       8586       8596       8606       8616       8626       8636
GCTGTGTTGG ACTTTTTCTA AGTGAGACCT GGAGTGAAAG AACTACCTAT TAATGAATTA GTAGGGAGGG 8646       8656       8666       8676       8686       8696       8706
HinfI
G|AGTCTTCTT AGCTGTGAAA ATTTTAGAGT TGCATTTGGT TCCATTAAAT GTGGTATTTC TTTCCACTAG
```

FIG. 7A pGLT104

```
           360        370        380        390        400        410        420
     TCATGGCGAC CACACCCGTC CTGTGGATCC TTGGCTGTTT TGCTTGAGTA AGGTATCTCA AGGTCTACAA
                                pBR327—><—Insert 430        440        450        460        470        480        490
     CAGCACCAGG CATGTAGTAG GTACTCCAGT AAATATTTCT TGAGTGAAAG AATCAATTCG TACCACAATA 500        510        520        530        540        550        560
     TTATGAGGAA CACACAATTA TTTTTCTTTT TCAGACAATA AAGCTGAAAC TTAGACAATA TACATAATGT 570        580        590        600        610        620        630
     ATTAAAGGTC ACACTACTTG TAATGGAATA ACTTGGATTC CAATCCAAGC CTTCTCCCTA GAGCTTACAC 640        650        660        670        680        690        700
     CCACTACTCC ACCCCCACTG GTGTTTGCCA GCATTGGATG AGGGAGAGGA AGATTCTGAA ACGAGGGAGG 710        720        730        740        750        760        770
     AAATAGGAAG GTGGAGAAGG GGCTAGAAAT AAATCTCTGT GTGCCAAGCT AAGCAGTTTA AACTACATTC 780        790        800        810        820        830        840
     CATAGCAGAA CCTCTGAATT GAATAGTGAC ATAATTAAAT CTGTATCTTA GAAAGATAAT TCAAAGAGCT 850        860        870        880        890        900        910
     GCTAACTGGA AAAGCGAAAG CCAACAAAAT GCTAGTGGAA AGAAATACCA CATTTAATGG AACCAAATGC 920        930        940        950        960        970        980
     AACTCTAAAA TTTTCACAGC TAAGAAGACT CCCCTCCCTA CTAATTCATT AATAGGTAGT TCTTTCACTC 990       1000       1010       1020       1030       1040       1050
     CAGGTCTCAC TTAGAAAAAG TCCAACACAG CATAAGTAGT TGTGAACTTA CACTTTATTC ATATATATTA 1060       1070       1080       1090       1100       1110       1120
     GATATTGATA ATTTTAACAA ATGAGTTACT TTCCATTTGG GTACAGTCAC AGTTGTCAAC AATATTTGGA 1130       1140       1150       1160       1170       1180       1190
     AGCACCAGGC ATGAAATCTC CTGAGATGCT ATGTTTTCAT CAGGGTCACC TGACACATTC AAGTCAGTTA 1200       1210       1220       1230                              1252
     CCTATCGGA AAGAAAAGAG CAAAATTAAT TTCAGGCATA TAAGCCA TCA GGA TAT TCT GCT
                                                     .   reS elI grA reS
                                                         <—intron 3 derived 1267                    1282                    1297
     AAT GTC ATG ATG GTC AGT GAC CGA ATA ATT AGT CAG CTT TTC GAA GTC ATC TCG
     elI psA siH siH psA rhT laV reS ryT nsA rhT ueL syL ulG ehP psA psA grA
     residues———>

FIG. 7B

```
          1312                    1327                    1342                    1357
TTT CTT TTT GTT GCT ATT GAA AAA CTT GAC ATT CAT GTC TTC CTT GAT GGT CTC
Lys Lys Lys Asn Ser Asn Phe Phe Lys Val Asn MET Asp Glu Lys Ile Thr Glu 1372                    1387                    1402
CAC ACT CTT TTG GAT GCT CTG GTC ATC TTT AAA GTT TTT AAA AAG TTT GAA GTA
Val Ser Lys Gln Ile Ser Gln Asp Asp Lys Phe Asn Lys Phe Leu Lys Phe Tyr 1417                    1432                    1447                    1462
AAA GGA GAC AAT TTG GCT CTG CAT TAT TTT TCT GTC ACT CTC CTC TTT CCA ATT
Phe Ser Val Ile Gln Ser Gln MET Ile Lys Arg Asp Ser Glu Glu Lys Trp Asn
                                          exon 3 —> <— exon 2

1477                    1492                    1507                    1522
CTT CAA AAT GCC TAA GAA AAG AGT TCC ATT ATC CGC TAC ATC TGA ATG ACC TGC
Lys Leu Ile Gly Leu Phe Leu Thr Gly Asn Asp Ala Val Asp Ser His Gly Ala
                                                                      exon 1537                    1552                    1567
ATT AAA ATA TTT CTT AAG GTT TTC TGC TTC TTT TAC ATA TGG GTC CTG GCA GTA
Asn Phe Tyr Lys Lys Leu Asn Glu Ala Glu Lys Val Tyr Pro Asp Gln Cys Tyr
2 —> <— exon 1                                                        exon 1 —

1649        1659        1669        1679        1689        1699
ACA AGCTGTTTCC TGTGTGAAAT TGTTATCCGC TCACAATTCC ACACAACATA CGAGCCGGAA
Cys    <—>                                    ↑
  —>   Shine    <—operator complement—>     Start
       Dalgarno                              transcription
       complement 1709        1719        1729        1739        1749        1759        1769
GCATAAAGTG TAAAGCCTGG GGTGCCTAAT GAGTGAGGTA ACTCACATTA ATTGCGTTGC GCTCACTGCC
       <—>
       -35
       complement 1779        1789        1799        1809        1819        1829        1839
CGCTTTCCAG TCGGGAAACC TGTCGTGCCA GCTGGATTAA TGAATCGGCC AACGCGCGG GAGAGGCGGT 1849        1859        1869        1879        1889        1899        1909
TTGCGTATTG GGCGCCACGC TTCCCAAGG GAGAAAGGCG GACAGGTATC CGGTAAGCGG CAGGGTCCCA 1919        1929        1939        1949        1959        1969        1979
ACAGGAGAGC GCACGAGGGA GCTTCCAGGG GGAAACGCCT GGTATCTTTA TAGTCCTGTC GGGTTTCGCC
```

FIG. 7C

```
          1989       1999       2009       2019       2029       2039       2049
     ACCTCTGACT TGAGCGTCGA TTTTTGTGAT GCTCGTCAGG GGGGCGGAGC CTATGGAAAA ACGCCAGCAA 2059       2069       2079       2089       2099       2109       2119
     CGCGGCCTTT TTACGGTTCC TGGCCTTTTG CTGGCCTTTT GCTCACATGT TCTTTCCTGC GTTATCCCCT 2129       2139       2149       2159       2169       2179       2189
     GATTCTGTGG ATAACCGTAT TACCGCCTTT GAGTGAGCTG ATACCGCTCG CCGCAGCCGA ACGACCGAGC 2199       2209       2219       2229       2239       2249       2259
     GCAGCGAGTC AGTGAGCGAG GAAGCGGAAG AGCGCCAGGG TGGTTTTTCT TTTCACCAGC GAGACGGGCA 2269       2279       2289       2299       2309       2319       2329
     ACAGCTGATT GCCCTTCACC GCCTGGCCCT GAGAGAGTTG CAGCAAGCGG TCCACGCTGG TTTGCCCCAG 2339       2349       2359       2369       2379       2389       2399
     CAGGCGAAAA TCCTGTTTGA TGGTGGTTCC GAAATCGGCA AAATCCCTTA TAAATCAAAA GAATAGCCCG
                                                                        Insert—><—

2409
     PGCCGCGTTG
     pBR327
```

POLYPEPTIDE HAVING GAMMA-INTERFERON ACTIVITY LACKING AMINO ACIDS CODED BY EXON 4

This application is a continuation of application Ser. No. 614,130, filed on May 25, 1984, now abandoned.

TECHNICAL FIELD

The present invention is directed to a novel polypeptide having properties similar to naturally occurring human gammainterferon (IFN-γ). The present invention also relates to a novel plasmid capable of producing the novel polypeptide and a microorganism containing said plasmid.

BACKGROUND OF THE INVENTION

The gene in the human body which carries the genetic information responsible for the synthesis of gamma-interferon contains certain sequences of bases which code for the amino acid sequence of gamma-interferon (exons) and certain sequences which do not code for gamma-interferon (introns). In a human cell, the gamma-interferon gene creates RNA in the nucleus of the cell. This RNA contains both introns and exons. The introns, which do not code for a sequence of the gamma-interferon, are deleted to generate messenger RNA (mRNA). After the introns are deleted, the resulting mRNA directs the synthesis of natural gamma-interferon in the cytoplasm of the cell.

The amino acid sequence of human gamma-interferon has been identified, and DNA which codes for the gamma-interferon has been incorporated into, for example, E. coli which is capable of producing the gamma-interferon (See, European Patent Application Publication No. 0077670, published on 27 Apr. 1983).

SUMMARY OF THE INVENTION

The present invention relates to a novel polypeptide having human gamma-interferon activity which has an amino acid sequence which is different from naturally occurring human gamma-interferon as reported by Gray et al., Nature 295, 503 (1982). It has been surprisingly discovered that this polypeptide, which is enclosed by a polynucleotide lacking exon 4, possesses human gamma-interferon activity.

A radioactive probe was utilized to identify plaques from a bacteriophage lambda/human genomic library (gift from Professor T. Maniatis) containing the human gamma-interferon gene. One of the clones which appeared to contain the entire gamma-interferon gene on the basis of restriction enzyme analysis was cleaved with BamHI, and the fragment containing the gamma-interferon gene was ligated into BamHI-cleaved pBR327 (Soberon et al., Gene 9: 287 (1980)) to produce a new plasmid designated pCG5 (11.7 kb). This new plasmid was incorporated into a host microorganism to produce a transformed microorganism. pCG5 was then cleaved with MstII and SalI to excise a portion of extraneous DNA and religated to form a new plasmid pCG51 (8.7 kb). This plasmid was then further cleaved and a portion was ligated with a segment excised from pCG5 to produce a new plasmid pCG52 (6.4 kb). pCG52 in turn was cleaved and religated to yield another new plasmid pCG53 (5.6 kb). A segment from this plasmid was then inserted into a phage vector (M13mp9) and used to transfect E. coli. An attempt was made to delete introns 1, 2, and 3 from the phage containing the gamma-interferon gene. Unexpectedly, during the above procedure portions of the genetic material which code for gamma-interferon (portions of exons 1 and 4) were deleted. However, the deleted nucleotide sequence does not appear to be necessary for gamma-interferon activity. A phage capable of expressing a polypeptide having gamma-interferon activity was obtained by further genetic manipulation and utilized in E. coli to prepare a material having gamma-interferon activity.

The genetic sequence responsible for the production of this activity was excised from the M13mp9 bacteriophage derivative and inserted into pBR327 to prepare the plasmid pGLT104. Surprisingly, E. coli harboring this latter plasmid contains a polypeptide in the cytoplasm thereof which possesses gamma-interferon activity in a concentration which is approximately 4 to 10 times higher than the activity present in a microorganism utilized for comparison purposes which contains the entire gamma-interferon gene. Analysis of the nucleotide sequence of pGLT104 indicates that this polynucleotide contains a sequence of nine nucleotides which are the same as the first nine nucleotides of exon 4. However, these nine nucleotides are not derived from exon 4 but are derived from the deleter which is utilized to delete intron 3.

The present invention is therefore directed to a novel polypeptide having gamma-interferon activity wherein the portion of said polypeptide which is coded for by all but the first nine nucleotides of exon 4 is deleted. Thus, the polypeptide of the present invention contains a sequence of amino acids coded for by the last 18 amino acids of exon 1, exon 2, exon 3 and the first nine nucleotides of exon 4, respectively. In addition, the polypeptide contains an additional terminal sequence of amino acids which is coded for by a portion of the nucleotides of intron 3. Thus, the present invention is further directed to a polypeptide coded for by a nucleotide sequence in which a substantial thermal portion by exon 4 is deleted and is replaced with a nucleotide sequence derived from intron 3. The polynucleotide which codes for the polypeptide is representable by the general formula (a terminal portion of exon 1) (exon 2)-(exon 3)-(an initial portion of exon 4)-(a portion of intron 3), (the last fifty-four nucleotides of exon 1)-(exon 2)-(exon 3)-(the first nine nucleotides of exon 4)-(twenty-four nucleotides derived from intron 3) or (Cys Tyr Cys Gln Asp Pro Tyr Val Lys Glu Ala Glu Asn Leu Lys Lys Tyr Phe)-(exon 2)-(exon 3)-(GTC ACT GAC)-(CAT CAT GAC ATT AGC AGA ATA TCC). The specific amino sequence of the polypeptide is shown in FIG. 7 by the amino acids coded for by nucleotides 1579 through 1241.

The invention is also directed to a novel polynucleotide sequence which codes for the new polypeptide and the complementary strand thereof, a novel replicable expression vehicle such as a plasmid containing said nucleotide sequence, a novel microorganism containing said plasmid, mutants of said microorganism and various intermediate products utilized in the preparation of said microorganism. For example, one aspect of the present invention is directed to a vector, such as a bacteriophage, which contains the nucleotide sequence of the present invention.

The present invention also is directed to a method for preparing the above-discussed plasmids and microorganisms, a method for preparing a polypeptide having gamma-interferon activity, and pharmaceutical compositions containing the polypeptide produced in accordance with the present invention. Genetic material capable of producing polypeptides having interferon activity in accordance with the present invention may be incorporated into various types of replicable expression vehicles that are compatible with different strains of bacteria, such as E. coli, or vehicles which are compatible with yeast, mammalian cells, or other cells capable of producing or encoding the polypeptide of the present invention after transformation.

BRIEF DESCRIPTION OF THE DRAWING

FIG. 4 shows the portion of the nucleotide sequence of pCG53 which contains the inserted gene of interest;

FIG. 5 summarizes the events leading to the nucleotide sequence of mp9-TGdl;

FIG. 6 shows the nucleotide sequence of mp9-TGΔ123-1; and

FIG. 7 shows the nucleotide sequence of pGLT104.

DESCRIPTION OF THE PREFERRED EMBODIMENT

Figure 1:
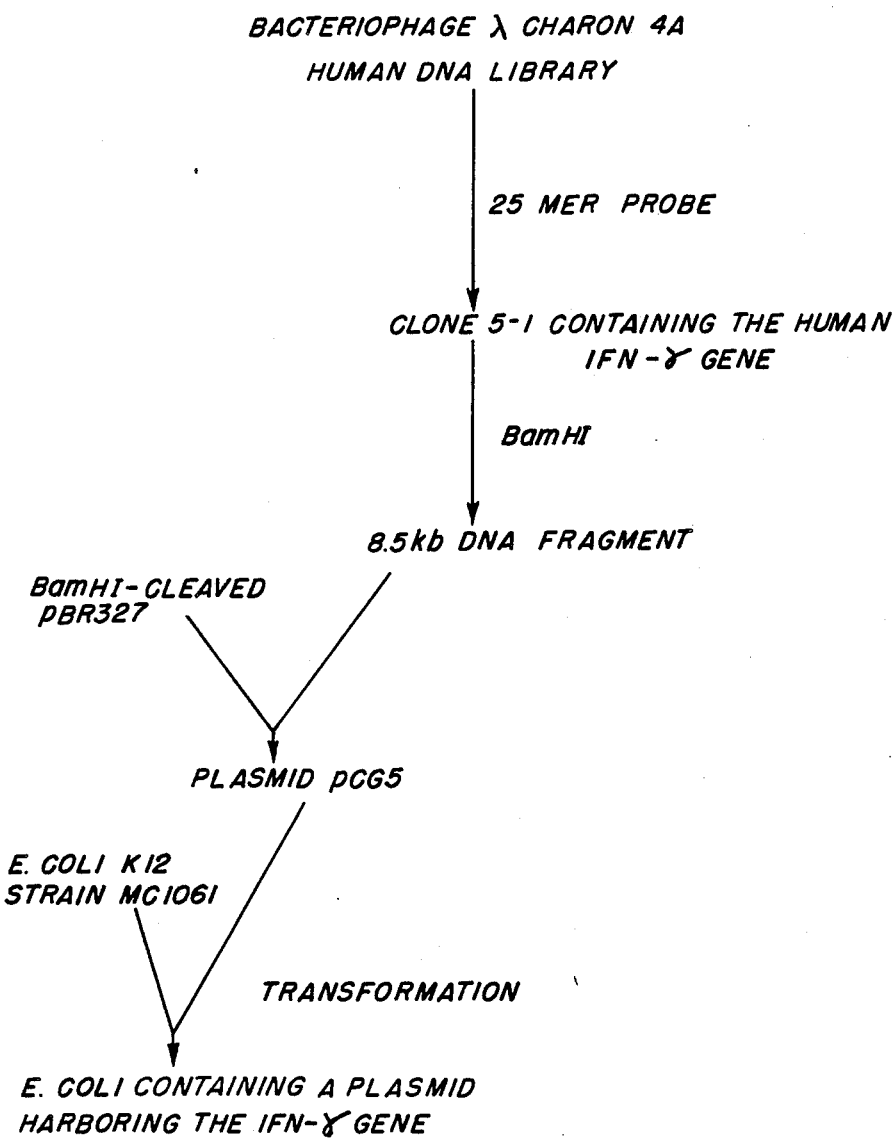
FIG. 1 is a flow chart showing construction of pCG5.

Synthesis of DNA Oligomers Using Nucleotide Monomers

To a stainless steel 500 µl reaction vessel with stainless steel filters at each end is added 20 mg of a polystyrene resin to which a nucleoside (2.0 µmoles) is connected via a succinate linkage. The resin is treated with zinc bromide (1M) in dichloromethane/isopropanol (85:15) to remove the dimethoxytrityl (DMT) protecting group, washed with dimethylformamide, pyridine, and acetonitrile, and dried with a stream of nitrogen. To the dried resin is added a solution of DMT-nucleotide (20 µM) and mesitylenesulfonylnitrotriazole (60 µM) in 200 µl pyridine. The coupling reaction is allowed to proceed at 45° C. for 20 minutes. This cycle of deprotection and coupling is repeated for successive nucleotides until the desired DNA oligomer has been assembled on the resin. The resin is then treated to remove the DNA oligomer from the resin and purified as described by Ito et al, (Nucl. Acids Res. 10: 1755 (1982)).

Isolation of the Human Genomic Gamma-Interferon Gene

As illustrated in FIG. 1, a $^{32}$P-labelled synthetic 25-mer oligonucleotide, 5'CCATTATCCGCTACATCTGAATGAC3', complementary to a sequence in exon 2, is used as a hybridization probe to screen $10^6$ plaques of bacteriophage Charon 4A/human genomic library prepared by insertion into the EcoRI ligation site of Charon 4A vector (Blattner et al., Science 196: 161 (1977)) sized fragments from EcoRI digested hhuman DNA (Maniatis et al., Cell 15: 687 (1978)). The plaque hybridization method of Benton et al, (Science 196: 180 (1977)) is used. Since not all of the bacteriophage in culture contain the necessary genetic material for preparing gamma-interferon a probe which has a base sequence complementary to the exon 2 portion of the gamma-interferon gene is used. Plaques having the desired genetic material are identified by the binding of the radioactive probes to their DNA. Two hybridizing plaques are isolated from the library. DNA from each recombinant phage is isolated and digested with five restriction endonucleases (EcoRI, BamHI, PvuII, HindIII, and HincII). Each phage DNA is analyzed by gel hybridization with the 25-mer probe, after digestions with the above enzymes. Comparison of these hybridization patterns with those of Gray et al, (Nature 298: 859 (1982)) indicates that one phage DNA (clone 5-1) appears to contain the entire gamma-interferon gene. Clone 5-1 is selected for further study.

Construction of Bacterial Clones Containing Human Genomic Gamma-Interferon Gene The method of Landy et al. (Biochemistry 13: 2134 (1974)) is used to obtain DNA of clone 5-1. This DNA is digested with BamHI and the digest is electrophoresed on 1% low melting agarose gel. The 8.5 kb band is isolated from the agarose gel as described by T. Maniatis (p. 377, Molecular Cloning, Cold Spring Harbor Laboratory, 1982). This fragment is cloned to BamHI-cleaved pBR327. The plasmid obtained is used to transform E. coli K12 strain MC1061. Ten bacterial clones are screened using the miniprep technique of Holmes et al, (Anal. Biochem. 114: 193 (1981)). In this way, a colony which contains the desired genomic segment is obtained. The plasmid DNA prepared from this colony is designated pCG5.

Construction of pCG53 Containing Human Mini-Genomic Gamma-Interferon Gene

Figure 2:
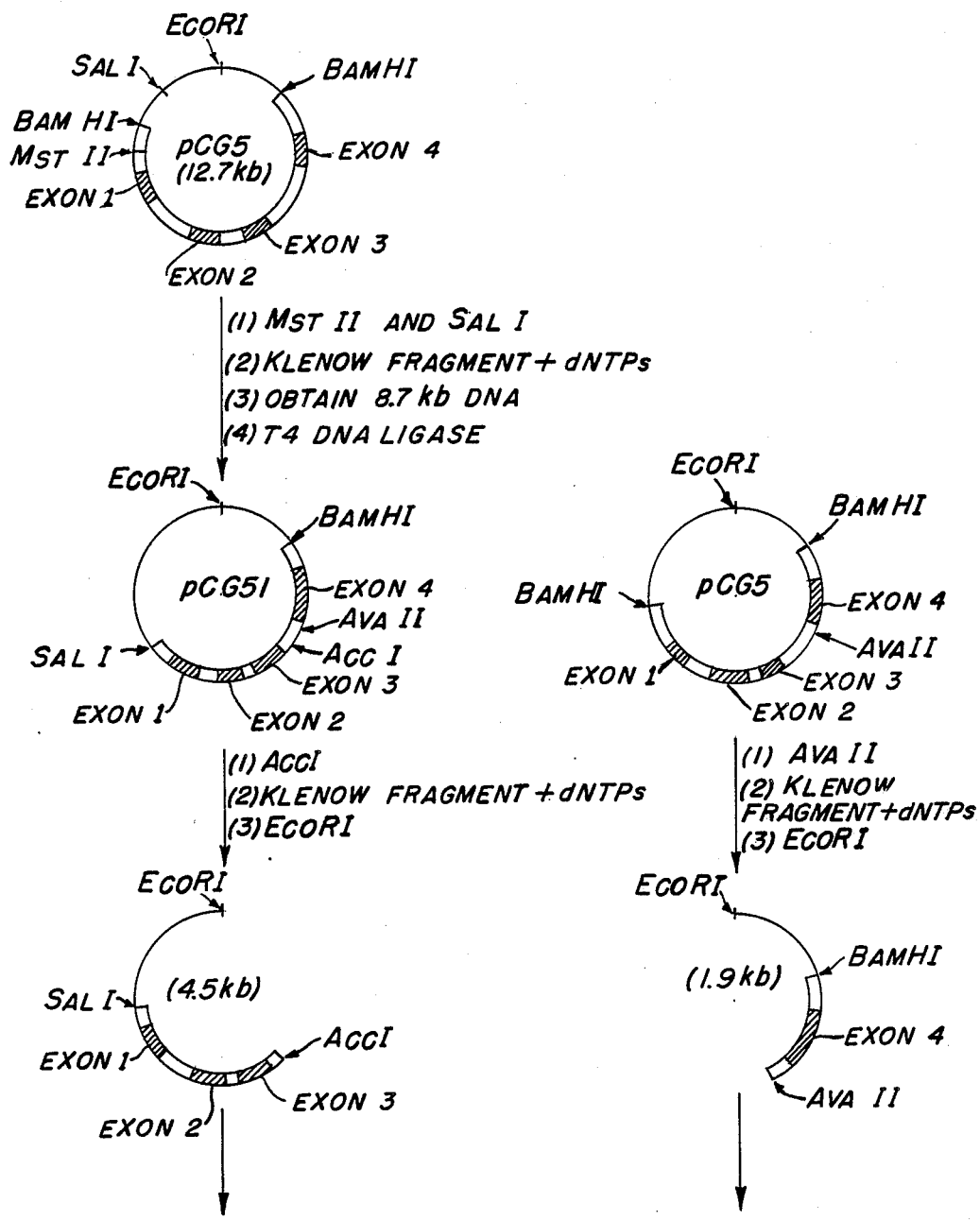
FIGS. 2 and 3 are a schematic diagram illustrating the construction of pCG53.
Figure 3:
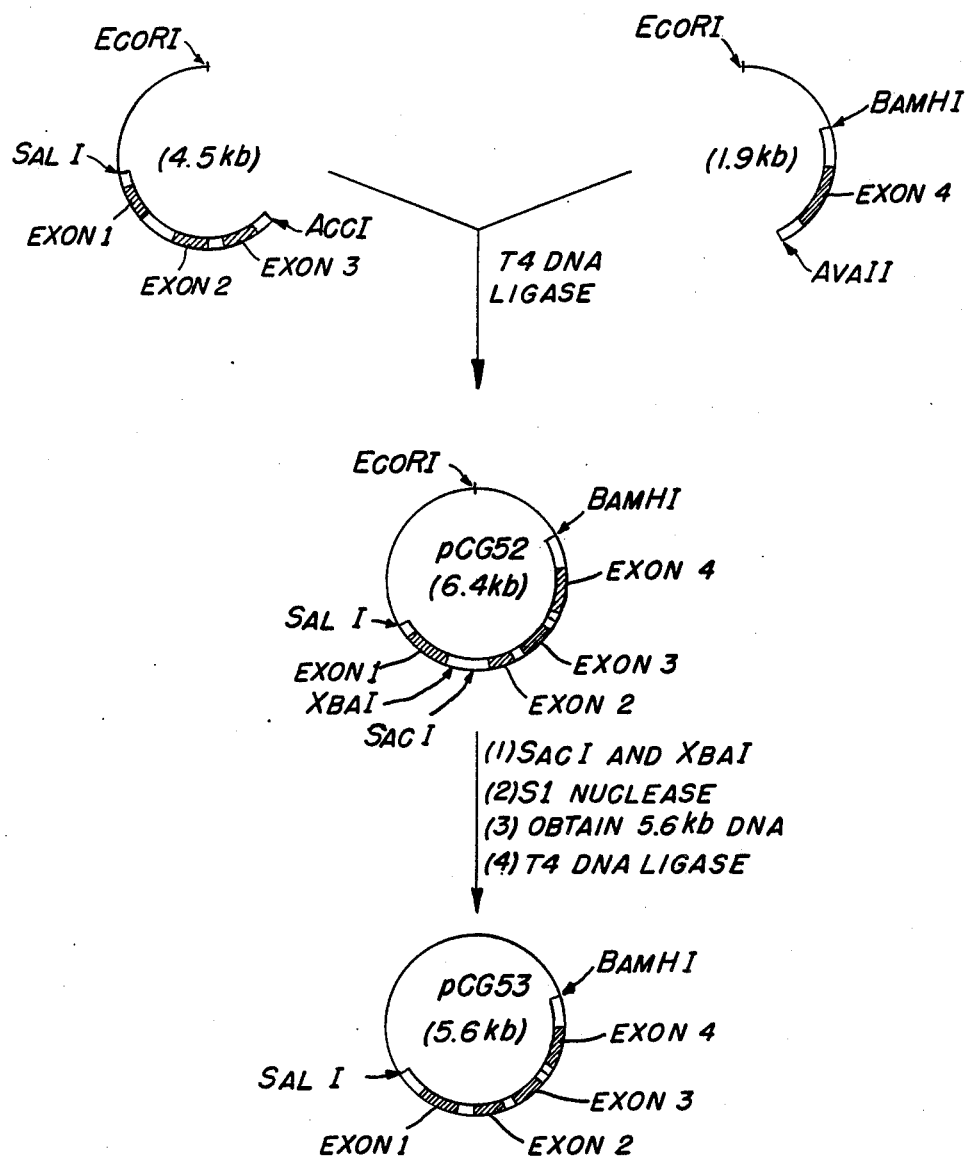

The DNA in the plasmid pCG5 is found to read in the counterclockwise direction. From pCG5, pCG53 is constructed as indicated in FIGS. 2 and 3. pCG5 (5 µg) is cut with MstII (5 units) and SalI (8 units). After digestion, the Klenow fragment of E. coli DNA polymerase I (14 units) is added, and the mixture is adjusted to 0.5 mM with dATP, dGTP, dCTP, and dTTP. The reaction is allowed to proceed for 5 minutes at room temperature. By this treatment, the single-stranded end of the fragment is filled in with the complementary nucleotides to form blunt double-stranded ends. After electrophoresis on 1% low melting agarose gel, the 8.7 kb size DNA is eluted. Two µg of this fragment is recovered. This fragment (60 ng) is treated with T4 DNA ligase (10 units) to ligate the ends of the fragment and form a circular product. The product is used to transform E. coli MC1061. In this way, 41 transformants are obtained. Unexpectedly, the plasmid DNA of one of these transformants has a SalI site located at the ligation site. The plasmid DNA from this clone is designated pCG51.

To the plasmid DNA (10 µg) (FIG. 2) of pCG51 clone is added AccI restriction enzyme (10 units). After digestion, the Klenow fragment of E. coli DNA polymerase (14 units) is added, and the mixture is adjusted to 0.5 mM with dATP, dGTP, dCTP and dTTP. The reaction is allowed to continue for 30 minutes at room temperature. The product is then digested with EcoRI (20 units). The final digest is electrophoresed on 1% low melting agarose gel, and 4.5 kb size DNA is eluted. The plasmid pCG5 (5 µg) is then digested with AvaII (10 units). After digestion, the Klenow fragment of E. coli DNA polymerase I (14 units) is added, and the reaction mixture is adjusted to 0.5 mM with dATP, dGTP, dCTP and dTTP. After reaction for 30 minutes at room temperature, the product is cut with EcoRI (10 units). After electrophoresis on 1% low melting agarose gel, 1.9 kb DNA is eluted. These two fragments (the 4.5 kb and the 1.9 kb fragments) are then ligated with T4 ligase for 2 hours at 15° C. The ligated product is used to transform E. coli MC10761 and E. coli D1210. The plasmid DNA isolated from the clones of the transformed E. coli is examined by restriction enzyme digestion. Plasmid DNA with the desired digestion pattern is obtained from a clone and designated pCG52. A culture of E. coli containing the plasmid pCG52 has been deposited with the American Type Culture Collection (ATCC) in Rockville, Md. in accordance with the provisions of the Budapest Treaty and has been given Deposit No. ATCC 39665. The plasmid pCG52 carries a gene coding for ampicillin resistance. E. coli containing this plasmid should be cultivated in L-broth containing 20 μg/ml ampicillin. The E. coli deposited at ATCC 39665 is a gram negative rod which is lac−, leu−, ara− and str$^r$.

pCG52 (50 μg) is cut with SacI (50 units) and XbaI (100 units), and the single-stranded ends are rendered blunt by digestion with S1 nuclease (2.9 units) for 5 minutes at 37° C. After electrophoresis on 1% low melting agarose gel, the 5.6 kb size DNA is eluted. Six μg of DNA is recovered. This DNA (100 ng) is circularized by treatment with T4 ligase (10 units) for 2 hours at 15° C. The circularized DNA is used to transform E. coli MC1061 and E. coli D1210. The plasmid DNA isolated from the clones of the transformed E. coli is examined by restriction enzyme digestion. Plasmid DNA with the desired digestion pattern is obtained from a clone and designated pCG53. The portion of the nucleotide sequence of pCG53 which contains the desired gene is shown in FIG. 4. A culture of E. coli containing the plasmid pCG53 has been deposited with the ATCC in accordance with the provisions of the Budapest Treaty and has been given Deposit No. ATCC 39666. This bacteria should be cultivated in the same manner as ATCC 39665. The E. coli deposited as ATCC 39666 is lac−, leu−, ara− and str$^r$.

Construction of M13mp9-TG2 Containing the Human Minigene for Gamma-Interferon from pCG53

Plasmid pCG53 (10 μg) is digested with SalI (20 units) and BamHI (20 units). After electrophoresis on 1% low melting agarose gel, the 2.6 kb fragment is eluted. This fragment is inserted into the BamHI/SalI fragment from the replicative form of M13mp9 phage. The product is transfected to E. coli JM103 (BRL User Manual/M13mp7 cloning/'Dideoxy' sequencing, 1980). The product is designated M13mp9-TG2.

Deletion of Introns 1, 2, and 3, Using M13mp9-TG2 Single Strand DNA and Deleters E1-2, E2-3, and E3-4

The single-strand DNA and M13mp9-TG2 is prepared by the method of BRL User Manual/M13mp7 cloning/'Dideoxy' sequencing, 1980. E1-2, (5'ACCTGCATTAAAATATTTCTTAAGG3'), is a deleter for intron 1. E2-3, (5'GTCACTCTCCTCTTTCCAATT3'), is a deleter for intron 2. E3-4, (5'GTCAGTTACCGAATAATTAGT3'), is a deleter for intron 3.

The deleters have a base sequence which is complementary to the base sequence of the bases before and after the intron to be deleted. Thus, the deleters should attach to the appropriate base sequences before and after the intron causing the intron to be deleted to loop out. Fill-in of the second strand comprising the deleters would delete the introns as described in Wallace et al., Science 209: 1396 (1980).

E1-2 (124 ng, 15 pmole), E2-3 (104 ng, 15 pmole) and E3-4 (104 ng, 15 pmole) are phosphorylated using T4 kinase (10 units) and ATP (3 mM) and are added to the template M13mp9-TG2 (1.65 μg, 0.5 pmole). The reaction mixture is heated at 65° C. for 5 minutes, cooled to room temperature for 5 minutes, and finally cooled in ice water. To dATP, dCTP, dGTP, dTTP and ATP (0.4 mM) is added Klenow fragment of E. coli DNA polymerase I (5 units), T4 DNA ligase (10 units) in Hin buffer (Wallace et al., Nuc. Ac. Res. 9: 3647 (1981)), 10 mM Tris.HCl (pH 7.2), 2 mM MgCl$_2$ and 1 mM beta-mercaptoethanol. The reaction mixture (final volume 50 μl) is incubated for 30 minutes at 4° C. and then for 30 minutes at room temperature. The DNA from the oligonucleotide-primed reaction is used to transfect E. coli JM103 by the procedure of the BRL User Manual/M13mp7 cloning/'Dideoxy' sequencing, 1980. From 2 μl of the 50 μl reaction volume, 10,000 plaques are obtained. From these, 150 plaques are picked to YT plates (J. H. Miller, p. 433, Experiments in Molecular Genetics, Cold Spring Harbor Laboratory (1972)). The colonies obtained are hybridized at 55° C. for 2 hours with $^{32}$P-labelled E1-2, E2-3, and E3-4. For this step the deleters are used as probes to identify sequences of DNA having the corresponding complementary base sequence after the introns have been deleted. The numbers of plaques out of the 150 plaques hybridizing with each of the three deleters or combinations of them are given below.

| | |
|---|---|
| E1-2 | 6 |
| E2-3 | 22 |
| E3-4 | 14 |
| E1-2 + E2-3 | 2 |
| E1-2 + E3-4 | 1 |
| E2-3 + E3-4 | 7 |
| E1-2 + E2-3 + E3-4 | 0 |

One of the two clones hybridizing with both E1-2 and E2-3, mp9-TGdl, is used in an attempted deletion of intron 3. Subsequent experiments indicate that the exon 4 portion of the DNA of mp9-TGdl is missing. The events leading to mp9-TGdl are summarized in FIG. 5. Deleter E3-4 (104 ng, 15 pmole) was kinased using T4 kinase (10 units) and ATP (3 mM). The template mp9-TGdl single strand DNA (1.6 μg, 0.5 pmole) is added, an the mixture is heated at 65° C. for 5 minutes, cooled at room temperature for 5 minutes, and then cooled in ice water. To a 0.4 mM solution of dATP, dCTP, dGTP, dTTP and ATP is added Klenow fragment of E. coli DNA polymerase I (5 units) and T4 DNA ligase (10 units) in Hin buffer and treated as described above. The resultant phage is plated, and 150 plaques are picked to YT plates. The clones are allowed to hybridize at 55° C. for 2 hours with $^{32}$P-labelled E3-4. Two positive clones, mp9-TGΔ123-1, and mp9-TGΔ123-2 are obtained. When clone mp9-TGΔ123-1 is sequenced, intron 1 is found to be completely deleted, but this clone does not hybridize with the 23-mer primer/mutator (5'GCAGGTCGACCATTACTGGGATG3') of which the terminal 19 nucleotides are complementary to the terminal 8 nucleotides of exon 4 and the 11 subsequent nucleotides. This result suggests that a portion of exon 4 is missing. Examination of mp9-TGdl reveals that this also does not complement the 23-mer primer mutator. Apparently a portion of exon 4 is lost prior to the second treatment with E3-4. The phage mp9-TGΔ123-1 has been deposited with the ATCC in accordance with the provisions of the Budapest Treaty and has been given deposit number ATCC 40117. The nucleotide sequence of the relevant portion of mp9-TGΔ123-1 is shown in FIG. 6. This phage can be grown under conditions which are normally used to cultivate M13mp9 phage. The ATCC deposit 40117 is a deposit of the phage in a lysate supernate.

Construction of mp9-TGd-Δ123-1 for Expression

The sequence between the ATG start codon at the termination of the promoter and the second cysteine codon of the gamma-interferon sequence is deleted fro mp9-TGdl using D-4 deleter, (5'GGTCCTGGCAG-TAACACATAGCTGTTTCC3'), by an analogous procedure to obtain mp9-TGΔ123-1. Sequencing confirms that deletion of the desired portion between the ATG start codon of the lac promoter and the second cysteine codon has been been achieved. As can be seen from FIG. 5, the D-4 deleter deleted the codons for the first 19 amino acids of exon 1.

Construction of pGLT104

The replicative form of mp9-TGΔ123-1 is digested with AvaI and BamHI. The fragment from the AvaI at position 5826 extending to the single BamHI site 3' to the interferon gene sequence is isolated and cloned to BamHI/AvaI-cleaved pBR327 to yield the plasmid pGLT104. The plasmid pGLT104 is incorporated into E. coli strains MC1061 and D1210. A culture of E. coli D1210 containing the plasmid pGLT104 has been deposited with the ATCC in accordance with the provisions of the Budapest Treaty and has been given Deposit Number ATCC 39667. The plasmid pGLT104 carries a gene coding for ampicillin resistance. A culture of E. coli containing this plasmid should be cultivated in L-broth containing 20 μg/ml ampicillin. The E. coli containing pGLT104 which is identified as ATCC 39667 is a gram negative rod which is lac$^-$, leu$^-$, ara$^-$ and str$^r$. The nucleotide sequence of pGLT104 is set forth in FIG. 7. The amino acid sequence of the polypeptide of the present invention is shown in FIG. 7. The polynucleotide sequence shown in FIG. 7 is the sequence of the complementary strand of DNA. The nucleotide sequence of the coding strand of the DNA is easily determined by determining the complementary nucleotides. Thus, the coding strand of the DNA has the nucleotide sequence GTC ACT GAC CAT CAT GAC ATT AGC AGA ATA TCC from nucleotides 1273 to 1241 whereas the corresponding complementary strand (reading in the 3' to 5' direction) has the sequence CAG TGA CTG GTA GTA CTG TAA TCG TCT TAT AGG. As shown in FIG. 7, the nucleotide base sequence "CAG TGA CTG" which begins at base pair 1273 has a sequence which is the same as the first nine nucleotides of the complementary strand of exon 4. As noted above, these nucleotides are derived from the E 3-4 deleter. Therefore, the resulting polypeptide having gamma-interferon activity lacks the amino acids coded by the terminal portion of exon 4 but instead contains a sequence of eight amino acids coded by twenty-four nucleotides derived from intron 3.

This clone has a BamHI site, but the AvaI site is no longer evidenced. E. coli containing pGLT104 is cultured in a conventional nutrient medium. Bioassay of the product of gamma-interferon activity indicates 4 to 10 times higher activity measured in terms of units/liter (u/l) than is obtained with a plasmid (pGLY102) containing the complete gamma-interferon gene under control of the lac promoter. Bioassay is conducted using a line (WISH) of human amnion cells by the procedure of Rubinstein et al. (J. Virology 37: 755 (1981)).

| | Exp. 1 | Exp. 2 |
|---|---|---|
| pGLY102 (E. coli MC1061) | $1.2 \times 10^3$ U/l | $5.0 \times 10^3$ U/l |
| pGLY102 (E. coli D1210) | $1.0 \times 10^4$ U/l | $7.6 \times 10^3$ U/l |
| pGLT104 (E. coli MC1061) | $1.0 \times 10^4$ U/l | — |
| pGLT104 (E. coli D1210) | — | $2.0 \times 10^4$ U/l |

Production of Polypeptide

E. coli containing a plasmid capable of coding for the polypeptide of the present invention (e.g., pGLT104) is inoculated into a conventional nutrient medium such as L-broth containing an antibiotic, a sugar source and essential vitamins. The culture is incubated until a sufficient quantity of interferon is produced by the E. coli. The E. coli cells are harvested by centrifugation and resuspended in a phosphate buffered saline solution. The cells are ruptured by sonication and the resulting solution is cleared by centrifugation. The interferon activity of the polypeptide is assayed in a conventional manner and the polypeptide is purified in a conventional manner.

Pharmaceutical Composition

Purified polypeptide is dissolved in a pharmaceutically acceptable carrier, excipient or diluent according to known methods in an amount sufficient to exhibit gamma-interferon activity when administered to a host. Suitable carriers and their formulations for the preparation of pharmaceutical compositions are described in Remington's *Pharmaceutical Sciences* by E. W. Martin, which is hereby incorporated by reference. The pharmaceutical compositions will contain an effective amount of the polypeptide of the invention in combination with a suitable amount of a carrier for proper administration to a host.

Practical Utility

The polypeptide is administered to a subject or host in a manner and in an amount sufficient to exhibit antitumor, antiviral or immunosuppressive activity. The amount and manner of administration is similar to that currently being employed in the art. The polypeptide of the invention may be administered to subjects requiring anti-tumor, or antiviral treatment, and to those patients exhibiting immunosuppressive conditions. Dosage and dose rate may vary according to the particular application but may essentially follow that currently in use in clinical investigations on humans with human interferon, e.g., about $(1-10) \times 10^6$ units daily, and in the case of materials having a purity greater than 1 percent, likely up to, e.g., $50 \times 10^6$ units daily. The dosages of the polypeptide could be significantly elevated for greater effect owing to the essential absence of contaminating proteins when produced by genetic engineering techniques.

The invention being thus described, it will be obvious that the same may be varied in many ways. Such variations are not to be regarded as a departure from the spirit and scope of the invention, and all such modifications as may be obvious to those skilled in the art are intended to be included within the scope of the following claims.

We claim:

1. A polypeptide having human gamma-interferon activity having the amino acid sequence Cys Tyr Cys Gln Asp Pro Tyr Val Lys Glu Ala Glu Asn Leu Lys Lys Tyr Phe Asn Ala Gly His Ser Asp Val Ala Asp Asn Gly Thr Leu Phe Leu Gly Ile Leu Lys Asn Trp Lys Glu Glu Ser Asp Arg Lys Ile Met Gln Ser Gln Ile Val Ser Phe Tyr Phe Lys Leu Phe Lys Asn Phe Lys Asp Asp Gln Ser Ile Gln Lys Ser Val Glu Thr Ile Lys Glu Asp Met Asn Val Lys Phe Phe Asn Ser Asn Lys Lys Lys Arg Asp Asp Phe Glu Lys Leu Thr Asn Tyr Ser Val Thr Asp His His Asp Ile Ser Arg Ile Ser 2. A pharmaceutical composition comprising an antitumor, antiviral or immunosuppressive effective amount of the polypeptide of claim 1 and a pharmaceutically acceptable carrier or diluent.

* * * * *